(12) United States Patent
Zervos

(10) Patent No.: US 6,841,347 B1
(45) Date of Patent: Jan. 11, 2005

(54) IN VIVO CONSTRUCTION OF DNA LIBRARIES

(75) Inventor: Antonis Zervos, Woburn, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/245,549

(22) Filed: Feb. 5, 1999

Related U.S. Application Data

(60) Provisional application No. 60/073,817, filed on Feb. 5, 1998.

(51) Int. Cl.[7] .......................... C12Q 1/68; C12P 19/34; C12N 1/20; C12N 5/00
(52) U.S. Cl. ...................... 435/6; 435/91.2; 435/252.3; 435/325
(58) Field of Search .................. 435/6, 91.2, 252.3, 435/325

(56) References Cited

U.S. PATENT DOCUMENTS

| | | | | |
|---|---|---|---|---|
| 4,683,202 A | | 7/1987 | Mullis | 435/91 |
| 4,870,023 A | * | 9/1989 | Fraser et al. | 435/320 |
| 4,966,841 A | | 10/1990 | Riley | 435/69.1 |
| 5,580,717 A | | 12/1996 | Dower et al. | 435/5 |
| 5,681,726 A | | 10/1997 | Huse et al. | 435/91.52 |
| 5,837,458 A | * | 11/1998 | Minshull et al. | 435/6 |
| 5,925,544 A | * | 7/1999 | Jorgensen | 435/69.1 |
| 5,928,868 A | * | 7/1999 | Liu et al. | 435/6 |
| 5,976,846 A | * | 11/1999 | Passmore et al. | 435/172.3 |

FOREIGN PATENT DOCUMENTS

| | | | | |
|---|---|---|---|---|
| WO | WO 95/34320 | 12/1995 | | A61K/39/00 |
| WO | WO 97/34633 | 9/1997 | | A61K/39/395 |

OTHER PUBLICATIONS

Andersson et al. Analytical Biochemistry, 1996, vol. 236, p. 107–113.*
Li et al. Nucleic Acids Research, 1997, vol. 25(20), p. 4165–4166.*
Aslanidis et al. PCR Methods and Applications, 1994, vol. 4(3) p. 172–177.*
Tillett et al. Nucleic Acids Research, 1999, vol. 27(19) e26 p. i–iii.*
Bartel et al., Analyzing Protein–Protein Interactions Using Two–Hybrid System, Methods of Enzymology, Acad. Press, 1995, 254:241–263.
Chien et al., "The Two–Hybrid System: A Method to Identify and Clone Genes for Proteins that Interact with a Protein of Interest", PNAS, 88:9578–9582.
Gyuris et al., "Cdi1, a Human G1 and S Phase Protein Phosphatase That Associates with Cdk2", Cell, 1993, 75:791–803.
Ma et al., "A New Class of Yeast Transcriptional Activators", Cell, 1987, 51:113–119.

* cited by examiner

*Primary Examiner*—Kenneth R. Horlick
*Assistant Examiner*—Joyce Tung
(74) *Attorney, Agent, or Firm*—Fish & Richardson P.C.

(57) ABSTRACT

The invention provides methods of preparing a plurality of nucleic acid insert molecules. The invention also provides methods of constructing a DNA library in vivo. A kit allowing the interchangeable use of a DNA library in more than one application is also provided. Finally, the invention provides a method for screening subjects for the existence of lesions in a gene encoding a particular protein.

24 Claims, 3 Drawing Sheets

IN VIVO CONSTRUCTION OF DNA LIBRARIES

This application claims the benefit of Provisional application Ser. No. 60/073,817, filed Feb. 5, 1998.

FIELD OF THE INVENTION

This invention relates to an intracellular method for malting DNA libraries.

BACKGROUND OF THE INVENTION

A cDNA library is a collection of cloned DNA molecules propagated in an appropriate host. It is usually derived from the mRNA population of a particular cell, tissue or organ by reverse transcription, cloned into a vector molecule and propagated in an appropriate host cell.

cDNA libraries are useful in numerous applications. cDNA libraries can be used to isolate and identify cell-specific expressed sequences. A cDNA clone isolated from a library can be sequenced and translated (e.g., by computer programs) to derive the primary amino acid sequence of the encoded protein or can be used as a labeled probe to investigate gene expression in vivo.

cDNA libraries can also be used in a two-hybrid assay to screen a large number of candidate proteins and identify those which interact with a particular target protein. In this approach, cDNAs are incorporated into activation domain vectors to provide random proteins fused to an activation domain of a known transcription factor. Vectors encoding the target protein fused to the DNA binding domain of the transcription factor, and the library of activation domain hybrids are cotransformed into a reporter strain. Interaction of the target protein moiety of a target protein DNA binding domain fusion protein with a protein encoded by cDNA brings the DNA binding domain into proximity with the activation domain fused to the cDNA encoded protein. The resulting transcription identifies a positive clone. Once a positive clone has been identified, the gene corresponding to the interacting protein can be isolated and analyzed.

The use of cDNA libraries has become increasingly widespread and, as a result, the need for methods which allow the rapid construction of cDNA libraries in vectors appropriate for particular applications is imperative.

SUMMARY OF THE INVENTION

In general, the invention features, a method for constructing a DNA library, e.g., a cDNA library, in vivo. The method includes:

providing a plurality of host cells;

providing a vector having a first region and a second region;

providing a plurality of nucleic acid insert molecules having a first common region which is homologous with the first region of the vector, a second common region which is homologous with the second region of the vector, and a library element encoding region disposed between the first common region and the second common region, wherein when the library element encoding region encodes a naturally occurring sequence, the first and second common regions are not naturally found adjacent to the library element encoding region (the term "common" means that each molecule of the plurality includes the common sequence);

introducing a vector molecule into each of the host cells;

introducing a nucleic acid insert molecule into each of the cells, wherein a different library element encoding region is introduced into each of the cells; and allowing homologous recombination and gap repair between the vector molecule and the nucleic acid insert molecule to occur, thereby constructing a DNA library.

In preferred embodiments, the DNA library can be a cDNA library, a genomic DNA library, or a synthetic DNA library.

In preferred embodiments, homologous recombination and gap repair occurs between the vector molecule and the nucleic acid insert molecule.

In preferred embodiments, the first and the second common regions can be the same or can be different. The first and the second common regions can be all or part of a linker used for the creation of an existing cDNA library, or they can be all or part of a site the library element encoding region had been inserted in. For example, the first and the second common regions can be all or part of a vector, e.g., all or part of a polylinker region, or part of a naturally occurring sequence existing adjacent to the library element encoding region, e.g., all or part of a gene, such as a conserved sequence within a gene, e.g., a zinc finger motif, a helix loop helix motif, or a WW domain.

In preferred embodiments, the second region of the first and the second primers can be the same or can be different. The second region of the first and the second primers can be homologous to a vector sequence, e.g., a polylinker site or a sequence which flanks the insertion site, or can be homologous to a sequence in a different nucleic acid insert molecule, e.g., a nucleic acid insert molecule intended to be part of a final construct including a plurality of nucleic acid insert molecules. For example the second region of the first and the second primers can be homologous to a restriction enzyme cleavage site, e.g., a Not I, an EcoR I, or a Hind III cleavage site.

In preferred embodiments, the second region of the first primer is 5' to the first region of the primer. In preferred embodiments, the second region of the second primer is 3' to the first region of the primer.

In preferred embodiments, the host cell can be a yeast cell, e.g., a *Saccharomyces cerevisiae* or *Schizosaccharomyces pombe* cell, a bacterial cell, e.g., an *E. coli* cell, such as, for example, the *E. coli* strains CJ236, NM522, 5K, TGE7300, JM101, JM107, KM392 or LE392, or a mammalian cell, such as, for example, a CHO, COS, C127, or a HepG2 cell.

In preferred embodiments, the vector can be linearized prior to being introduced into the host cell. For example, the vector can be linearized by cleaving between the first and second regions of the vector. Examples of vectors which can be used in the methods of the invention include λgt10, λgt11, the ZAP series vectors (Stratagene), pESP-1, pOPRSV1MSC, pGAD.GH, pVP16, pACT, pGAD424, pGAD2F, or pJG4-5.

In preferred embodiments, the second region of the nucleic acid insert molecule is produced by PCR, using primers having a first region which is homologous to the 3' end of the element encoding region and a second region which is homologous to the second region of the vector. In preferred embodiments, the first region of the nucleic acid insert molecule is produced by PCR, using primers having a first region which is homologous to the 5' end of the element encoding region and a second region which is homologous to the first region of the vector.

In preferred embodiments, the second region of the nucleic acid insert molecule is produced by the ligation of adapters having a sequence homologous to the second region of the vector. In preferred embodiments, the first region of the nucleic acid insert molecule is produced by the ligation of adapters having a sequence homologous to the first region of the vector.

In preferred embodiments, the first and second regions of the nucleic acid insert molecule can be at least 20, 30, 40, 50, 60 or more base pairs in length. In preferred embodiments, the first and second common sequences of the nucleic acid insert molecule can be at least 20, 30, 40, 50, 60 or more base pairs in length.

In preferred embodiments, the library element encoding region can be obtained from an existing cDNA library, e.g., a plasmid based cDNA library or a phage based cDNA library; an mRNA molecule, e.g., an mRNA molecule derived from a tissue, e.g., a cancerous tissue, such as, for example, prostate cancer tissue; or a DNA molecule, e.g., a naturally occurring DNA molecule or a synthetic DNA molecule. The library element encoding region can be a gene or a part thereof, for example, a promoter, a protein encoding region, a translational terminator or a transcriptional terminator, or an intragenic sequence, e.g., an intragenic sequence which encodes, for example, a transcriptional enhancer or silencer. In preferred embodiments, the library element encoding region is obtained from a few cells, e.g., less than 10, 100, or 1,000 cells (i.e. which contain less than 100, 1,000, or 10,000 pg of RNA.

In preferred embodiments, the vector further includes an element encoding a detectable agent, e.g., a member of a binding pair, e.g., a member of a ligand/counter-ligand pair, an antigen, a detectable enzyme, e.g., a beta-galactosidase, an alkaline phosphatase, a horseradish peroxidase, or a luciferase gene, which is, for example, fused with the library element encoding region, such that the library element encoding region can be detected.

In preferred embodiments, the DNA library can be screened in a two-hybrid system or it can be used for screening and cloning novel genes. In preferred embodiments, the vector can include a transcription factor activation domain and the method can further include introducing into the host cell a nucleic acid molecule encoding a hybrid protein, wherein the hybrid protein comprises a transcription factor DNA-binding domain attached to a test protein; introducing into the host cell a detectable gene, wherein the detectable gene comprises a regulator site recognized by the DNA-binding domain and wherein the detectable gene expresses a detectable protein when the test protein interacts with a protein encoded by the DNA library; plating the host cell onto selective media; and selecting for the host cell containing a DNA encoded protein which interacts with test protein.

In another aspect, the invention features, a method of preparing a plurality of nucleic acid insert molecules. The method includes:
  providing a plurality of nucleic acid molecules wherein each of the nucleic acid molecule includes, in order from 5' to 3', a first common sequence, a library element encoding region, and a second common sequence (the term "common" means that each molecule of the plurality includes the common sequence);
  providing a plurality of first primers, each of the first primers having a first region homologous with the first common sequence of the nucleic acid molecule and having a second region which is not homologous with the first (and preferably second) common sequence;
  providing a plurality of second primers, each of the second primers having a first region homologous with the second common sequence of the nucleic acid molecule and having a second region which is not homologous with the second (and preferably first) common sequence;
  forming a reaction mixture which includes the plurality of nucleic acid molecules, the plurality of the first primers, and the plurality of the second primers, under conditions which provide, e.g., by primer directed synthesis, a plurality of nucleic acid insert molecules having the following structure, in order from 5' to 3', a second region of the first primer/the first common region/a library element encoding region/the second common region/a second region of the second primer, thereby preparing a plurality of nucleic acid insert molecules.

In preferred embodiments, the first and the second common sequences can be the same or can be different. The first and the second common sequences can be all or part of a linker used for the creation of an existing cDNA library, or they can be all or part of a site the library element encoding region had been inserted in. For example, the first and the second common sequences can be all or part of a vector, e.g., all or part of a polylinker region, or part of a naturally occurring sequence existing adjacent to the library element encoding region, e.g., all or part of a gene, such as a conserved sequence within a gene, e.g., a zinc finger motif, a helix loop helix motif, or a WW domain.

In preferred embodiments, the second region of the first and the second primers can be the same or can be different. The second region of the first and the second primers can be homologous to a vector sequence, e.g., a polylinker site or a sequence which flanks the insertion site, or can be homologous to a sequence in a different nucleic acid insert molecule, e.g., a nucleic acid insert molecule intended to be part of a final construct including a plurality of nucleic acid insert molecules. For example the second region of the first and the second primers can be homologous to a restriction enzyme cleavage site, e.g., a Not I, an EcoR I, or a Hind III cleavage site.

In preferred embodiments, the second region of the first primer is 5' to the first region of the primer. In preferred embodiments, the second region of the second primer is 3' to the first region of the primer.

In preferred embodiments, the second region of the nucleic acid insert molecule is produced by PCR, using primers having a first region which is homologous to the 3' end of the element encoding region and a second region which is homologous to the second region of the vector. In preferred embodiments, the first region of the nucleic acid insert molecule is produced by PCR, using primers having a first region which is homologous to the 5' end of the element encoding region and a second region which is homologous to the first region of the vector.

In preferred embodiments, the second region of the nucleic acid insert molecule is produced by the ligation of adapters having a sequence homologous to the second region of the vector. In preferred embodiments, the first region of the nucleic acid insert molecule is produced by the ligation of adapters having a sequence homologous to the first region of the vector.

In preferred embodiments, the first and second regions of the nucleic acid insert molecule can be at least 20, 30, 40, 50, 60 or more base pairs in length. In preferred embodiments, the first and second common sequences of the nucleic acid insert molecule can be at least 20, 30, 40, 50, 60 or more base pairs in length.

In preferred embodiments, the library element encoding region can be obtained from an existing cDNA library, e.g., a plasmid based cDNA library or a phage based cDNA library; an mRNA molecule, e.g., an mRNA molecule derived from a tissue, e.g., a cancerous tissue, such as, for example, prostate cancer tissue; or a DNA molecule, e.g., a naturally occurring DNA molecule or a synthetic DNA molecule. The library element encoding region can be a gene or a part thereof, for example, a promoter, a protein encoding region, a translational terminator or a transcriptional terminator; or an intragenic sequence, e.g., an intragenic sequence which encodes, for example, a transcriptional enhancer or silencer. In preferred embodiments, the library element encoding region is obtained from a few cells, e.g., less than 10, 100, or 1,000 cells (i.e. which contain less than 100, 1,000, or 10,000 pg of RNA.

In another aspect, the invention features, a method of constructing a DNA library, e.g., a cDNA library. The method includes:

providing a plurality of nucleic acid molecules wherein each of the nucleic acid molecule includes, in order from 5' to 3', a first common sequence, a library element encoding region, and a second common sequence (the term "common" means that each molecule of the plurality includes the common sequence);

providing a plurality of first primers, each of the first primers having a first region homologous with the first common sequence of the nucleic acid molecule and having a second region which is not homologous with the first (and preferably second) common sequence;

providing a plurality of second primers, each of the second primers having a first region homologous with the second common sequence of the nucleic acid molecule and having a second region which is not homologous with the second (and preferably first) common sequence;

forming a reaction mixture which includes the plurality of nucleic acid molecules, the plurality of the first primers, and the plurality of the second primers, under conditions which provide, e.g., by primer directed synthesis, a plurality of nucleic acid insert molecules having the following structure, in order from 5' to 3', a second region of the first primer/the first common region/a library element encoding region/the second common region/a second region of the second primer;

providing a plurality of host cells;

providing a vector having a first region which is homologous with the second region of the first primer, and a second region which is homologous with the second region of the second primer, introducing a vector molecule into each of the host cells; and introducing one or more of the nucleic acid insert molecules into each of the cells under conditions which allow for recombination and gap repair, thereby providing a DNA library.

In preferred embodiments, the DNA library can be a cDNA library a genomic DNA library, or a synthetic DNA library.

In preferred embodiments, homologous recombination and gap repair occurs between the vector molecule and the nucleic acid insert molecule.

In preferred embodiments, the first and the second common sequences can be the same or can be different. The first and the second common sequences can be all or part of a linker used for the creation of an existing cDNA library, or they can be all or part of a site the library element encoding region had been inserted in. For example, the first and the second common sequences can be all or part of a vector, e.g., all or part of a polylinker region, or part of a naturally occurring sequence existing adjacent to the library element encoding region, e.g., all or part of a gene, such as a conserved sequence within a gene, e.g., a zinc finger motif, a helix loop helix motif, or a WW domain.

In preferred embodiments, the second region of the first and the second primers can be the same or can be different. The second region of the first and the second primers can be homologous to a vector sequence, e.g., a polylinker site or a sequence which flanks the insertion site, or can be homologous to a sequence in a different nucleic acid insert molecule, e.g., a nucleic acid insert molecule intended to be part of a final construct including a plurality of nucleic acid insert molecules. For example the second region of the first and the second primers can be homologous to a restriction enzyme cleavage site, e.g., a Not I, an EcoR I, or a Hind III cleavage site.

In preferred embodiments, the second region of the first primer is 5' to the first region of the primer. In preferred embodiments, the second region of the second primer is 3' to the first region of the primer.

In preferred embodiments, the host cell can be a yeast cell, e.g., a *Saccharomyces cerevisiae* or *Schizosaccharomyces pombe* cell, a bacterial cell, e.g., an *E. coli* cell, such as, for example, the *E. coli* strains CJ236, NM522, 5K, TGE7300, JM101, JM107, KM392 or LE392, or a mammalian cell, such as, for example, a CHO, COS, C127, or a HepG2 cell.

In preferred embodiments, the vector can be linearized prior to being introduced into the host cell. For example, the vector can be linearized by cleaving between the first and second regions of the vector. Examples of vectors which can be used in the methods of the invention include λgt10, μgt11, the ZAP series vectors (Stratagene), pESP-1, pOPRSV1MSC, pGAD.GH, pVP16, pACT, pGAD424, pGAD2F, or pJG4-5.

In preferred embodiments, the second region of the nucleic acid insert molecule is produced by PCR, using primers having a first region which is homologous to the 3' end of the element encoding region and a second region which is homologous to the second region of the vector. In preferred embodiments, the first region of the nucleic acid insert molecule is produced by PCR, using primers having a first region which is homologous to the 5' end of the element encoding region and a second region which is homologous to the first region of the vector.

In preferred embodiments, the second region of the nucleic acid insert molecule is produced by the ligation of adapters having a sequence homologous to the second region of the vector. In preferred embodiments, the first region of the nucleic acid insert molecule is produced by the ligation of adapters having a sequence homologous to the first region of the vector.

In preferred embodiments, the first and second regions of the nucleic acid insert molecule can be at least 20, 30, 40, 50, 60 or more base pairs in length. In preferred embodiments, the first and second common sequences of the nucleic acid insert molecule can be at least 20, 30, 40, 50, 60 or more base pairs in length.

In preferred embodiments, the library element encoding region can be obtained from an existing cDNA library, e.g., a plasmid based cDNA library or a phage based cDNA library; an mRNA molecule, e.g., an mRNA molecule derived from a tissue, e.g., a cancerous tissue, such as, for example, prostate cancer tissue; or a DNA molecule, e.g., a naturally occurring DNA molecule or a synthetic DNA molecule. The library element encoding region can be a gene or a part thereof, for example, a promoter, a protein encoding region, a translational terminator or a transcriptional terminator, or an intragenic sequence, e.g., an intragenic sequence which encodes, for example, a transcriptional enhancer or silencer. In preferred embodiments, the library element encoding region is obtained from a few cells, e.g., less than 10, 100, or 1,000 cells (i.e. which contain less than 100, 1,000, or 10,000 pg of RNA.

In preferred embodiments, the vector further includes an element encoding a detectable agent, e.g., a member of a binding pair, e.g., a member of a ligand/counter-ligand pair, an antigen, a detectable enzyme, e.g., a beta-galactosidase, an alkaline phosphatase, a horseradish peroxidase, or a luciferase gene, which is, for example, fused with the library element encoding region, such that the library element encoding region can be detected.

In preferred embodiments, the DNA library can be screened in a two-hybrid system or it can be used for screening and cloning novel genes. In preferred embodiments, the vector can include a transcription factor activation domain and the method can further include introducing into the host cell a nucleic acid molecule encoding a hybrid protein, wherein the hybrid protein comprises a transcription factor DNA-binding domain attached to a test protein; introducing into the host cell a detectable gene, wherein the detectable gene comprises a regulator site recognized by the DNA-binding domain and wherein the detectable gene expresses a detectable protein when the test protein interacts with a protein encoded by the DNA library; plating the host cell onto selective media; and selecting for the host cell containing a DNA encoded protein which interacts with test protein.

In another aspect, the invention features, a method of constructing a DNA library, e.g., a cDNA library, to be screened in a two-hybrid system. The method includes:

providing a plurality of nucleic acid molecules wherein each of the nucleic acid molecule includes, in order from 5' to 3', a first common sequence, a library element encoding region, and a second common sequence (the term "common" means that each molecule of the plurality includes the common sequence);

providing a plurality of first primers, each of the first primers having a first region homologous with the first common sequence of the nucleic acid molecule and having a second region which is not homologous with the first (and preferably second) common sequence;

providing a plurality of second primers, each of the second primers having a first region homologous with the second common sequence of the nucleic acid molecule and having a second region which is not homologous with the second (and preferably first) common sequence;

forming a reaction mixture which includes the plurality of nucleic acid molecules, the plurality of the first primers, and the plurality of the second primers, under conditions which provide, e.g., by primer directed synthesis, a plurality of nucleic acid insert molecules having the following structure, in order from 5' to 3', a second region of the first primer/the first common region/a library element encoding region/the second common region/a second region of the second primer, providing a plurality of host cells;

providing a vector having a first region which is homologous with the second region of the first primer, and a second region which is homologous with the second region of the second primer, wherein the vector further includes a transcription factor activation domain;

introducing a vector molecule into each of the host cells;

introducing one or more of the nucleic acid insert molecules into each of the cells under conditions which allow for recombination and gap repair to occur;

introducing into the host cell a nucleic acid molecule encoding a hybrid protein, wherein the hybrid protein includes a transcription factor DNA-binding domain attached to a test protein;

introducing into the host cell a detectable gene, wherein the detectable gene comprises a regulator site recognized by the DNA-binding domain and wherein the detectable gene expresses a detectable protein when the test protein interacts with a protein encoded by the DNA library;

plating the host cell onto selective media; and selecting for the host cell containing a DNA encoded protein which interacts with test protein.

In preferred embodiments, the DNA library can be a cDNA library a genomic DNA library, or a synthetic DNA library.

In preferred embodiments, homologous recombination and gap repair occurs between the vector molecule and the nucleic acid insert molecule.

In preferred embodiments, the first and the second common sequences can be the same or can be different. The first and the second common sequences can be all or part of a linker used for the creation of an existing cDNA library, or they can be all or part of a site the library element encoding region had been inserted in. For example, the first and the second common sequences can be all or part of a vector, e.g., all or part of a polylinker region, or part of a naturally occurring sequence existing adjacent to the library element encoding region, e.g., all or part of a gene, such as a conserved sequence within a gene, e.g., a zinc finger motif, a helix loop helix motif, or a WW domain.

In preferred embodiments, the second region of the first and the second primers can be the same or can be different. The second region of the first and the second primers can be homologous to a vector sequence, e.g., a polylinker site or a sequence which flanks the insertion site, or can be homologous to a sequence in a different nucleic acid insert molecule, e.g., a nucleic acid insert molecule intended to be part of a final construct including a plurality of nucleic acid insert molecules. For example the second region of the first and the second primers can be homologous to a restriction enzyme cleavage site, e.g., a Not I, an EcoR I, or a Hind III cleavage site.

In preferred embodiments, the second region of the first primer is 5' to the first region of the primer. In preferred embodiments, the second region of the second primer is 3' to the first region of the primer.

In preferred embodiments, the host cell can be a yeast cell, e.g., a *Saccharomyces cerevisiae* or *Schizosaccharomyces pombe* cell.

In preferred embodiments, the vector can be linearized prior to being introduced into the host cell. For example, the vector can be linearized by cleaving between the first and second regions of the vector. Examples of vectors which can be used in the methods of the invention include the "activation domain" vectors: pGAD.GH, pVP16, pACT, pGAD424, pGAD2F, or pJG4-5.

In preferred embodiments, the second region of the nucleic acid insert molecule is produced by PCR, using primers having a first region which is homologous to the 3' end of the element encoding region and a second region which is homologous to the second region of the vector. In preferred embodiments, the first region of the nucleic acid insert molecule is produced by PCR, using primers having a first region which is homologous to the 5' end of the element encoding region and a second region which is homologous to the first region of the vector.

In preferred embodiments, the second region of the nucleic acid insert molecule is produced by the ligation of adapters having a sequence homologous to the second region of the vector. In preferred embodiments, the first region of the nucleic acid insert molecule is produced by the ligation of adapters having a sequence homologous to the first region of the vector.

In preferred embodiments, the first and second regions of the nucleic acid insert molecule can be at least 20, 30, 40, 50, 60 or more base pairs in length. In preferred embodiments, the first and second common sequences of the nucleic acid insert molecule can be at least 20, 30, 40, 50, 60 or more base pairs in length.

In preferred embodiments, the library element encoding region can be obtained from an existing cDNA library, e.g., a plasmid based cDNA library or a phage based cDNA library; an mRNA molecule, e.g., an mRNA molecule derived from a tissue, e.g., a cancerous tissue, such as, for example, prostate cancer tissue; or a DNA molecule, e.g., a naturally occurring DNA molecule or a synthetic DNA molecule. The library element encoding region can be a gene or a part thereof, for example, a promoter, a protein encoding region, a translational terminator or a transcriptional terminator; or an intragenic sequence, e.g., an intragenic sequence which encodes, for example, a transcriptional enhancer or silencer. In preferred embodiments, the library element encoding region is obtained from a few cells, e.g., less than 10, 100, or 1,000 cells (i.e. which contain less than 100, 1,000, or 10,000 pg of RNA.

In preferred embodiments, the vector further includes an element encoding a detectable agent, e.g., a member of a binding pair, e.g., a member of a ligand/counter-ligand pair, an antigen, a detectable enzyme, e.g., a beta-galactosidase, an alkaline phosphatase, a horseradish peroxidase, or a luciferase gene, which is, for example, fused with the library element encoding region, such that the library element encoding region can be detected.

In another aspect, the invention features, a kit allowing the interchangeable use of a DNA library in more than one application, e.g., for easy and rapid transfer of a library insert from a first vector to a second vector. The kit includes one or more of the primers described herein, e.g., a plurality of first oligonucleotide primers, each of the first primers having a first region homologous with a first region common to all inserts, e.g., all or part of a linker used in the construction of the DNA library in the first vector, and a second region homologous with a first region of a second vector; a plurality of second oligonucleotide primers, each of the second primers having a first region homologous with a second region common to all inserts, e.g., all or part of a linker used in the construction of the DNA library in the first vector, and a second region homologous with a second region of a second vector, and optionally any of a reaction buffer, or DNA enzyme, e.g., a ligase or a restriction endonuclease, and instructions for use.

In preferred embodiments the kid includes one or more of: the library, e.g., a cDNA library; the library inserted into a first vector, the second vector into which the library is to be inserted.

In another aspect, the invention features, an oligonucleotide primer described herein, e.g., an oligonucleotide primer having a first region homologous with a linker sequence used in the construction of a DNA library, and a second region homologous with an insertion region of a vector required for a second application.

In another aspect, the invention features, a method for screening a subject for the existence of a lesion in a gene encoding a preselected protein. The method includes:

obtaining a tissue sample from the subject;

preparing from the tissue, a plurality of nucleic acid insert molecules having a first common region, a library element encoding region and a second common region, wherein the library element encoding region encodes the protein or portion thereof (the term "common" means that each molecule of the plurality includes the common sequence);

providing a vector having a first region which is homologous to the first common region of the nucleic acid insert molecule and a second region which is homologous to the second common region of the nucleic acid insert molecule, wherein the vector is suitable for use in an assay which detects the interaction between two proteins;

providing a host cell suitable for use in an assay which detects the interaction between two proteins;

introducing into the host cell the nucleic acid insert molecule, and the vector; and performing the assay which detects the interaction between two proteins, thereby screening subjects for the existence of lesions in the gene encoding the protein.

In preferred embodiments, the plurality of the nucleic acid insert molecules can be prepared by PCR using a first and a second primer, the first primer having a first region including the first region of the nucleic acid insert molecule and a second region homologous with a sequence in the library element encoding region, and the second primer having a first region including the second region of the nucleic acid insert molecule and a second region homologous with a sequence in the library element encoding region. In preferred embodiments, the assay which detects the interaction between two proteins can be a two-hybrid assay.

As used herein, the term "homologous recombination" refers to the process by which a DNA molecule can recombine (cross over) into a homologous sequence in another DNA molecule in, for example, a host cell. Homologous recombination can be catalyzed by enzymes called recombinases. Examples of recombinases include RecA, RecBCD, RAD51, or DMC1. Homologous recombination occurs frequently in bacteria, yeast, and certain viruses, as well as in some mammalian cells.

As used herein, the term "gap repair" refers to the process by which a host cell (e.g., a yeast cell) repairs double stranded breaks in a DNA molecule through homologous recombination.

As used herein, the term "homology" refers to a degree of sequnce identity between the nucleic acid sequence of two DNA molecules, sufficient to allow homologous recombination between the two DNA molecules to occur. The two DNA molecules can be, for example, at least 80, 90 or 100% identical.

As used herein, the term "library element encoding region" refers to a nucleic acid sequence or molecule which is the functional part of a nucleic acid insert molecule, e.g., a reverse transcription product of reverse transcription of an mRNA molecule. A library element encoding region can be, for example, a gene or a part thereof, e.g., a promoter, a protein encoding region, a translational terminator or a transcriptional terminator; or an intragenic sequence, e.g., an intragenic sequence which encodes, for example, a transcriptional enhancer or silencer. A library element encoding region can be obtained from an existing cDNA library, e.g., a plasmid based cDNA library or a phage based cDNA library; an mRNA molecule, e.g., an mRNA molecule derived from a tissue, e.g., a cancerous tissue, such as, for example, prostate cancer tissue; or a DNA molecule, e.g., a naturally occurring DNA molecule or a synthetic DNA molecule.

As used herein, the term "DNA library" refers to a collection of DNA molecules, e.g., cDNA, genomic DNA, or synthetic DNA molecules, cloned into a suitable vector. The cloned DNA molecules can be propagated in an appropriate host cell, e.g., a bacterial cell, and can be used in applications, such as, for example, the identification and cloning of novel genes. Examples of DNA libraries include genomic libraries, e.g., a liver or brain cell genomic library; or cDNA libraries, e.g., a human B cell or liver cell cDNA library.

The method of the invention is a highly efficient, rapid, cost effective alternative to current cDNA library construction methods. This method allows the rapid construction and screening of cDNAs, even from extremely small amounts of mRNA and it provides a universal way to screen cDNAs in the two hybrid system that can use all the different cDNA libraries currently available, independent of the vectors they are in. The method of the invention can, in many applications, replace conventional cDNA library construction methods.

Other features and advantages of the invention will be apparent from the following detailed description, and from the claims.

DETAILED DESCRIPTION

The drawings are first briefly described.

Vectors

Figure 1:
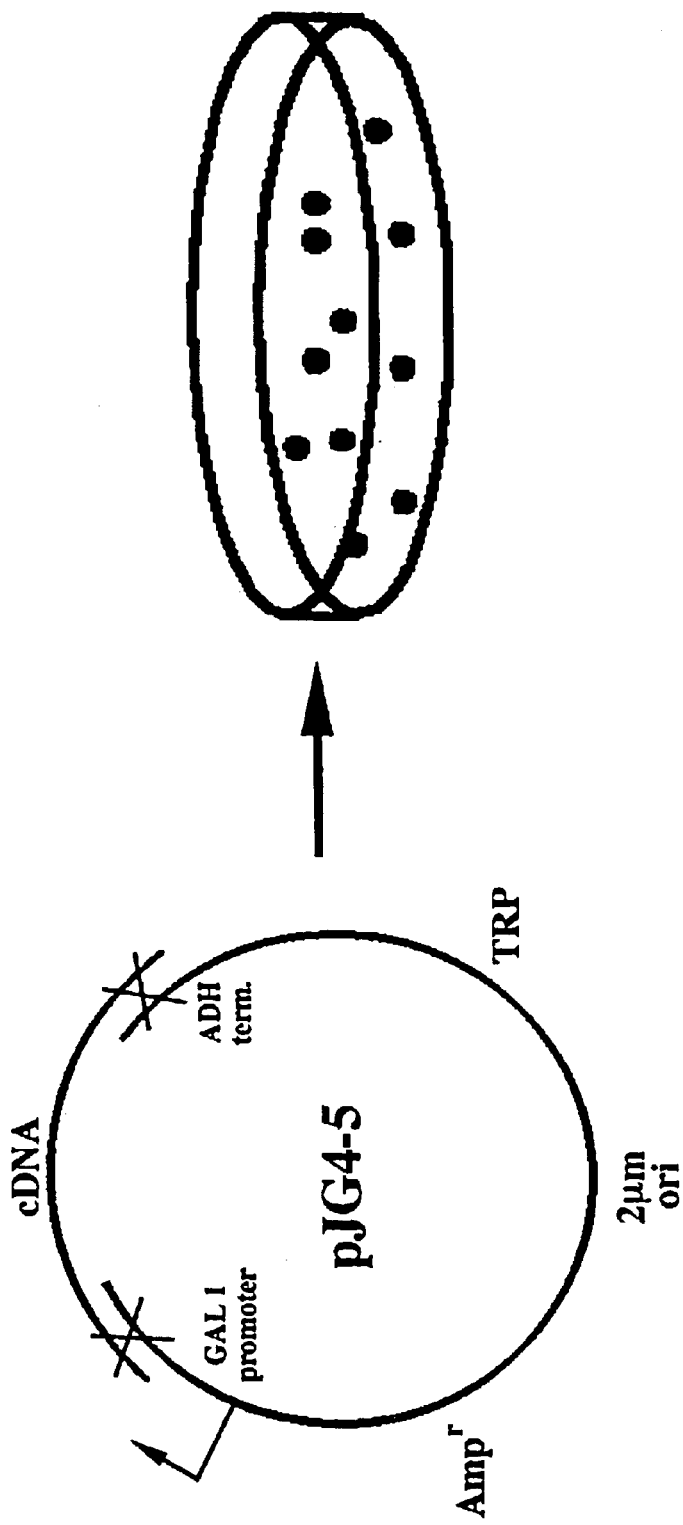
FIG. 1 is a schematic diagram of the method used for the in vivo construction of cDNA libraries (the gap repair process). Linear vector is cotransformed into yeast together with cDNA that has 5' and 3' end vector sequences added to its corresponding ends. By plating onto selective media, yeast colonies appear that have successfully integrated the cDNA into the plasmid through homologous recombination and gap repair.

Vectors usually include a backbone and site at which an insert can, or is, inserted. In many cases the insertion site will be flanked by one or more short regions which allow for cleavage by a predetermined restriction enzyme. After cleavage of the vector with such an enzyme, the vector has single strand overhangs which can hybridize with appropriate single stranded ends on an insert, the single stranded ends of which have been formed by cleavage with a predetermined enzyme. Preferred vectors are those capable of autonomous replication. Preferred vectors can direct expression of inserted nucleic acids. Vectors capable of directing the expression of genes to which they are operatively linked are often referred to as expression vectors. Plasmids, a term which refers generally to circular double stranded DNA loops which, in their vector form are not bound to the chromosome, are useful in the methods of the invention. In the present specification, plasmid and vector are used interchangeably as the plasmid is the most commonly used form of vector. However, methods of the invention include such other forms of vectors which serve equivalent functions.

Vectors can include selectable markers, promoters, and nucleic acids which encode proteins which are to be fused with the protein encoded by an insert.

Numerous vectors exist for the expression of DNA libraries, in both eukaryotic and prokaryotic cells. Examples of such vectors include λgt10, λgt11, the ZAP series (Stratagene), pESP-1, pOPRSV1MSC and the like. Vectors suitable for use in the two hybrid system are described below. In methods of the invention, the vector of interest is linearized prior to introduction into the host cell. The vector can be linearized by cleavage with an appropriate restriction enzyme. The procedures concerning the use of restriction enzymes, their nucleotide specificity and the appropriate reaction conditions are known to those skilled in the art and readily available. The amounts of enzyme and DNA, the buffer and ionic concentrations, and the temperature and duration of the reaction will vary depending upon the specific application as described in Sambrook et al. (*Molecular Cloning: A Laboratory Manual. 2nd, ed.*, Cold Spring Harbor Laboratory, Cold Spring Harbor Laboratory Press, Cold Spring Harbor, N.Y., 1989), and other laboratory manuals.

Host Cells

Cells which can support homologous recombination are suitable for use as host cells. Such cells include cells which have been genetically engineered to support homologous recombination.

Yeast cells, for example, *Saccharomyces cerevisiae* or *Schizosaccharomyces pombe* are suitable host cells. Strains of yeast that are of particular interest to the present invention include the two-hybrid system reporter strains Y153, containing the GAL1-HIS3 and GAL1-lacZ reporters and the trp1 and leu2 transformation markers, (Bartel et al., Methods in Enzymology, 254:241–263, 1995) CTY1, containing the GAL1-HIS3 and GAL1-lacZ reporters and the his3, trp1 and leu2 transformation markers (Chien et al., PNAS 88: 9578, 1991), CTY10-5d, containing the lexA-lacZ reporters and the his3, trp1, and leu2 transformation markers (Chien et al., PNAS 88: 9578, 1991), YBP2, containing the GAL1-HIS3 and (GAL17mers)-lacZ reporters and the trp1 and leu2 transformation markers (Chien et al., PNAS 88: 9578, 1991), and GGY1::171, containing the GAL1-lacZ reporter and the his3 and leu2 transformation markers (Gill at al., Cell 51:113, 1987).

Bacterial cells can also be used as host cells. *E. coli* cells, such as the *E. coli* strains CJ236 (Kunkel et al., 1987), NM522 (Gough and Murray, 1983), 5K and TGE7300 (Degryse, 1991b), JM101, JM107, KM392 or LE392, which have recombinational activity can be used. *Bacillus subtilis* cells, which have recombinational activity may also be used. A wide variety of mammalian cells, such as CHO, COS, C127, and HepG2 cells, as well as certain viruses, in which recombination occurs, can also be used.

Appropriate conditions for the growth of host cells, such as types of media (both liquid and solid), temperature and duration of incubation are known in the art, see, e.g., Sambrook et al. and in "Culture of Animal Cells. A Manual of Basic Technique", Freshney R. I., Third Edition, Wiley-Liss 1994. Methods for isolating discrete cell colonies or plaques, as well as plasmid DNA from such colonies or plaques are known in the art, and include plating the cells on selective media so that colonies or plaques are formed, lysing the cells by detergents, removing proteins by protease treatment, and purification of plasmid DNA through a CsCl gradient. The latter step can also be performed using commercially available DNA binding matrices in the form of columns (e.g., Qiagen Kit).

A nucleic acid insert molecule and vector can be introduced into prokaryotic or eukaryotic cells by any suitable methods e.g., by transformation or transfection. As used herein, the term "transformation" refers to methods for introducing foreign nucleic acid molecules (e.g., DNA) into a bacterial host cell. As used herein, the term "transfection" refers to methods for introducing foreign nucleic acid molecules (e.g., DNA) into a mammalian host cell. Methods for introducing a nucleic acid molecule into a host cell include "heat shock" transformation, calcium phosphate or calcium chloride co-precipitation, DEAE-dextran-mediated transfection, lipofection, or electroporation. For yeast cells, treatment with lithium acetate or lithium chloride, presents another alternative for efficient transfection. Suitable methods for transforming or transfecting host cells can be found in Sambrook, et al.

Library Element Encoding Region

A library element encoding region can be derived from a variety of sources. For example, a library element encoding region can be derived from tissue mRNA, an existing cDNA library (e.g. plasmid or phage based) or a naturally occurring or synthetic DNA molecule. Only a small amount of the starting material is needed. In fact, when the library element encoding region is derived from tissue mRNA, mRNA from one or a few cells, (e.g., less than 10, 100, or 1,000 cells) is sufficient to produce a DNA library. This is particularly useful when heterogeneous tissue populations are used. Such heterogeneous tissue populations include cancer tissues. For example, using laser techniques a few cells can be separated from a cancerous prostate tissue. Using these cells and the methods of the invention, described below, cDNA libraries of cancerous prostate cells can be produced rapidly.

Figure 3:
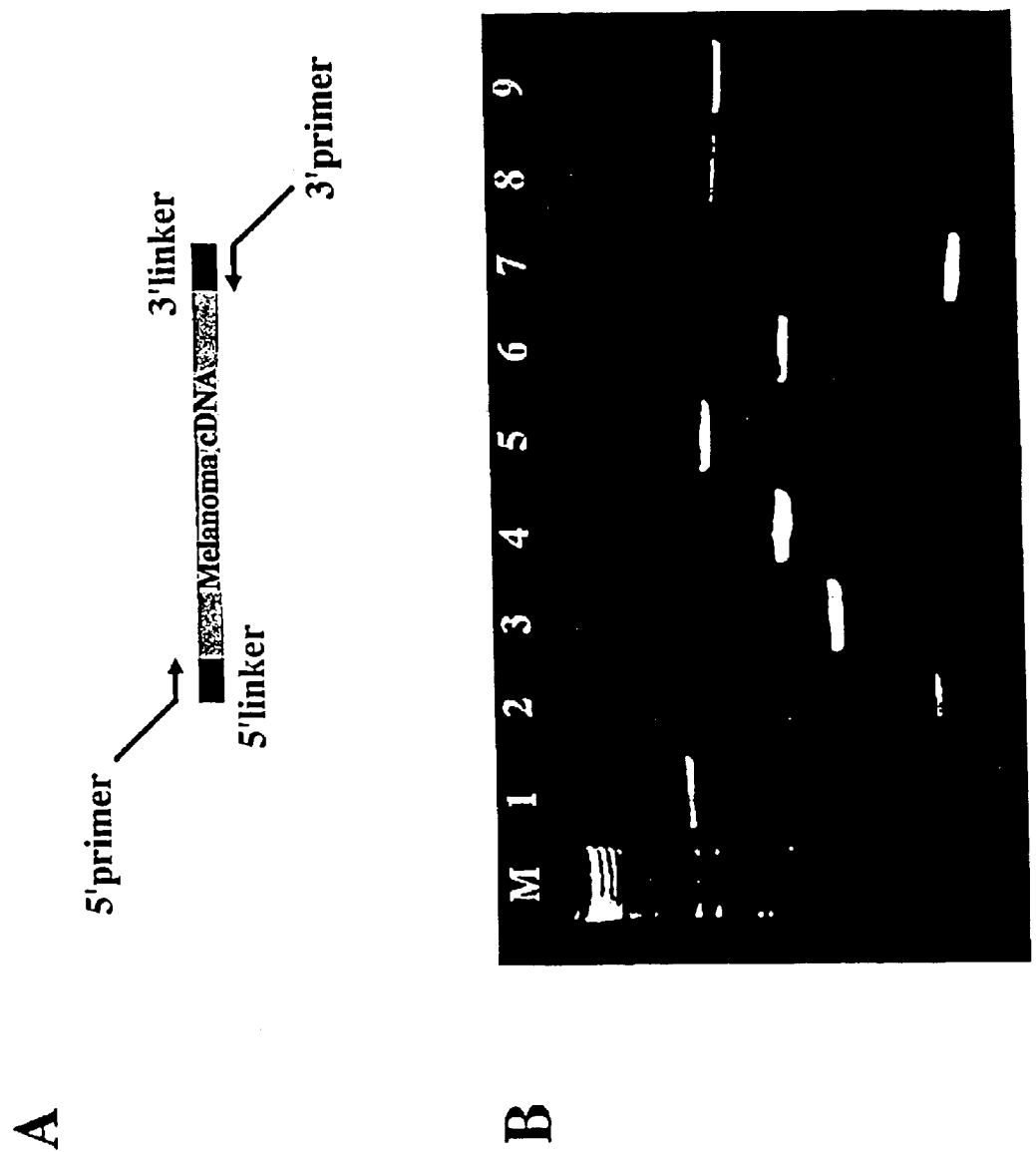
FIG. 3A is a schematic diagram of the commercially available cDNA (Marathon-Ready cDNA, Clonetech) used to determine the applicability of the cDNA cloning process.
FIG. 3B is a depiction of an agarose gel analysis and size characterization of the different cDNAs cloned in vivo. The data was obtained from nine randomly picked yeast colonies.

An existing DNA library, e.g., a cDNA library, can also be used as the source of library element encoding regions. A wide variety of cDNA libraries are available. Methods of the invention allow use of a library, designed for one application, in order to produce another library suitable for use in a different application, with very little experimental manipulation and effort. This can be achieved by simply using primers, e.g., PCR primers, containing a first region homologous with the nucleotide sequence in the linkers used during the construction of the existing cDNA library and a second region homologous with either a first or a second region in a vector, e.g., the terminal ends of the vector, appropriate for a particular application (see FIG. 3A).

A synthetic DNA molecule can be used as the source of the library element encoding region. For example, methods which generate populations of non-identical nucleic acid molecules, e.g., PCR with low fidelity Taq polymerase, can be used to generate library element encoding regions. These can be used in a two-hybrid assay, described below, in order to screen and identify, for example, proteins with a better affinity for a particular substrate.

Preparation of Nucleic Acid Insert Molecules

Nucleic acid insert molecules of the invention include a first region, a library element encoding region and a second region. The first and second regions have sufficient homology with a vector molecule such that homologous recombination can occur between a nucleic acid insert molecule and a vector molecule. The first and second regions flanking a nucleic acid insert molecule can be produced by PCR, using primers having a first and second region homologous with a first and second region in the vector, respectively. The use of PCR is known in the art and is described in U.S. Pat. No. 4,683,202, the contents of which are expressly incorporated herein by reference. The technique is also described in several general sources, see, e.g., Sambrook et al. and "PCR Protocols, A Guide to Methods and Applications" (Innis et al. eds.), Academic Press, San Diego, Calif., 1990. The Taq polymerase (Promega) and more preferably, either the Pfu (Stratagene) or Vent (New England Biolabs) polymerases can be used. The latter two have a proofreading ability and can, therefore, eliminate the introduction of errors in the PCR product during amplification. The resulting PCR products (i.e., the nucleic acid insert molecule), can be isolated by agarose or acrylamide gel electrophoresis followed by elution of the nucleic acid insert molecule from the agarose or acrylamide matrix. The two most common ways of elution are either soaking in an appropriate buffer or electroelution, both described in Sambrook et al. Both methods are effective, but soaking is often the method of choice because it is inexpensive, easy and can be accomplished without monitoring. Kits for the purification of DNA from gel matrices may also be used (e.g., "Compass Kit" by American Bioanalytical). The resulting nucleic acid insert molecule, can also be purified using reverse phase or anion-exchange HPLC.

The primer oligonucleotides, used in the PCR reaction, may be synthesized using commercially available solid phase oligonucleotide synthesis machines (Needham-VanDevanter, D. R., et al., *Nucleic Acids Res.*, 12:6159–6168, 1984), or chemically synthesized using the solid phase phosphoramidite triester method described by Beaucage et al., (Beaucage et al., *Tetrahedron Letts.* 22, No. 20:1859–1862, 1981). Oligonucleotides are preferably purified prior to use. Purification of oligonucleotides can be performed using reverse phase or anion-exchange HPLC and may also be carried out by denaturing or native polyacrylamide gel electrophoresis.

The first and second regions of a nucleic acid insert molecule, having homology to a vector, can be added to a library element encoding region by the ligation of adapters, having a sequence homologous to the terminal ends of the vector. As used herein, the term "adapter" refers to a, preferably short, double stranded DNA sequence, which can be linked to the ends of another DNA molecule. The adapter can be a synthetic DNA molecule, e.g., synthesized using a solid phase phosphoramidite triester method, or it can be a natural DNA molecule, e.g., produced by digestion using the appropriate restriction endonucleases. The adapter can be joined to the library element encoding region by ligation. Taq DNA ligase, the *E. coli* DNA ligase, or more preferably, T4 DNA ligase can be used.

The first and second regions of the nucleic acid insert molecule (i.e. the regions flanking the library element encoding region) can be of any size which supports an acceptable frequency of recombination, the size of the homologous region between the nucleic acid insert molecule and the vector sequences, usually being linear to the frequency of recombination. However, a minimum of 30 bp is preferred for efficient recombination to occur (see FIG. 2). Preferably, the first and second regions of the nucleic acid insert molecule have a length of at least 30, 40, 50, or 60 bp.

Methods of the invention can be used to produce DNA libraries from tissue mRNA. In such cases, the first and second regions of the nucleic acid insert molecule (flanking the library element encoding region) can be added directly during the library element encoding region synthesis from mRNA. Nucleic acid insert molecules can be synthesized from mRNA, using a first primer having a first region homologous with the polyT sequence of the mRNA, and a second region homologous with a first region in a vector of interest. First, intact mRNA is hybridized to the first primer. The mRNA is then copied by reverse transcriptase to produce an RNA-DNA hybrid, which can be isolated by standard methods (e.g., chloroform extraction and ethanol precipitation). The RNA from the RNA-DNA hybrid can be removed with the enzyme RNaseH, and an $E.$ $coli$ DNA polymerase I can be added to fill in the gaps and produce a double stranded DNA molecule which contains in its 3' end the second region of the first primer (which is homologous with a first region in a vector of interest). An adapter containing a region homologous to a second region in the vector of interest can then be added, e.g., ligated to, the 5' end of the library element encoding region, as described above. The resulting nucleic acid insert can then be introduced into an appropriate host cell, along with the vector, e.g., the linearized vector of interest.

An existing cDNA library, for example, a phage or plasmid based library, can also be the source of the library element encoding region. Existing libraries generally have a cDNA or other library element encoding region inserted between a first and second common sequence, e.g., a first and a second linker sequence. In such cases, a first and a second oligonucleotide primer can be designed to contain a first region homologous to the common sequence, i.e. the linkers used during the construction of the existing cDNA library and a second region homologous with a first and a second region in a vector of interest, respectively (see FIG. 3A). These primers can be used in a PCR amplification reaction to produce nucleic acid insert molecules which contain a first and a second region homologous with a first and a second region in the vector of interest, respectively. Both the vector and the nucleic acid insert molecule can be introduced into a host cell, as described above. Through homologous recombination and gap repair the host allows the nucleic acid insert molecule to be inserted into the vector, to thereby produce a new DNA library.

A population or library of DNAs can be modified in terms of content. For example, the population or library can be enriched for molecules having particular sequence motifs by amplification or subtractive methods. For example, degenerate primers can be used that selectively amplify a particular subset of DNAs, such as DNAs which encode proteins with zinc finger motifs, helix-loop-helix domains, WW domains, leucine zipper domains, and the like. Oligonucleotide primers can be synthesized to contain a first region homologous with a conserved nucleotide sequence present in the particular subset of DNA to be amplified, and a second region homologous with either a first or a second region in the vector molecule of interest. Such conserved nucleotide sequences are those present, for example, in genes which encode proteins with zinc finger motifs (e.g., Cys-Xaa2-Cys-Xaa1-3-Cys-Xaa2-Cys), (SEQ ID NO:12) WW domains (e.g., Pro-Xaa-Xaa-Trp-$X_{1-10}$-O-Trp-Xaa-Xaa-Pro) (SEQ ID NO:13) or the G protein alpha subunits from cochlear tissues (Tachibana et al., Hear Res 62:82–8, 1992).

As described above, these primers can be used in a PCR amplification reaction to produce a nucleic acid insert molecule, the nucleic acid insert molecule and a vector molecule can be introduced into a host cell, and through homologous recombination and gap repair, the nucleic acid insert molecule can be inserted into the vector, to produce a DNA library.

A DNA library can also be produced by the introduction of a plurality of nucleic L acid insert molecules and a vector molecule into a host cell. For example, three nucleic acid insert molecules (1–3) can be introduced into the host cell along with the vector of interest. Each nucleic acid insert molecule has a first and a second region. The vector also has a first and a second region. The first nucleic acid insert molecule has a first region homologous with the first region of the vector and a second region homologous with the first region of the second nucleic acid insert molecule. The second nucleic acid insert molecule has a first region homologous with the second region of the first nucleic acid insert molecule and a second region homologous with the first region of the third nucleic acid insert molecule. The third nucleic acid insert molecule has a first region homologous with the second region of the second nucleic acid insert molecule and a second region homologous with the second region of the vector. The regions are sufficiently homologous so as to allow homologous recombination and gap repair to occur between the nucleic acid insert molecules and the vector, once these are introduced into a host cell.

In Vivo DNA Libraries and the Two-Hybrid Assay

DNA libraries produced by homologous recombination and gap repair, e.g., in yeast, can be used for screening of expressed proteins using the two-hybrid system, (described in U.S. Pat. No. 5,283,317 and WO94/10300, the contents of which are incorporated herein by reference), in order to identify proteins, which bind to or interact with a protein of interest. The two-hybrid system is based on the use of a transcription factors, having a "modular" nature, i.e., having separable DNA-binding and activation domains. Briefly, the assay utilizes two different DNA constructs. In one construct, the gene that codes for a protein of interest ("bait") is fused to a gene encoding the DNA binding domain of a known transcription factor (e.g., GAL-4). In the other construct, the cDNA library, which encodes an unidentified protein ("prey" or "sample") is fused to a gene which codes for the activation domain of the known transcription factor. If the "bait" and the "prey" proteins are able to interact, in vivo, forming a complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein interacting with the protein of interest.

Examples of yeast vectors which are useful for the methods of the invention include the "activation domain" vectors: pGAD.GH, pVP16, pACT, pGAD424, pGAD2F and pJG4-5. Important features of these vectors are the ADH1 promoter which drives the expression of either the GAL4 activation domain, the $E.$ $coli$ B42 activator, or the herpes virus VP16 gene, and the ADH1 terminator. Also included in these vectors, are the $2\mu$ yeast origin of replication, an $E.$ $coli$ origin of replication, an $E.$ $coli$ selectable marker for ampicillin resistance, and yeast selectable markers, such as LEU2 or TRP1.

The in vivo cloning process can also be used to make DNA libraries for use in an application other than the two-hybrid assay. Such applications, include screening of a DNA library, by hybridization with a nucleic acid or an antibody probe in order to clone and identify novel genes. The screening procedure is usually performed on bacterial colonies, containing plasmids, or on bacteriophage plaques. In the case that the DNA library is constructed in yeast, the yeast colonies can be pooled and the library plasmids rescued en masse, following successful gap repair. The plasmids can then be used to transform bacteria, plated out and screened using radioactive probes or antibodies.

The methods of the invention can be used in the context of the two-hybrid system to screen patients (e.g., cancer patients) for lesions in a gene encoding a particular protein (e.g., Mxi1). For example, using tissue from a prostate cancer, a set of nucleic acid insert molecules can be produced as described above. These nucleic acid insert molecules can then be transformed into a yeast reporter strain along with a vector containing the activation domain of the Max protein. Mxi1 mutants unable to interact with Max will be unable to drive expression of the reporter gene, present in the yeast reporter strain, and as a result yeast cells will be unable to grow in a particular selective medium. By comparing the growth on plates lacking the selection marker versus the growth on plates including the selection marker, colonies containing an Mxi1 mutant can be identified. The afore-mentioned procedure can be used to screen patients suffering from any state or condition in which, a lesion in a gene encoding a particular protein might affect its interaction with another protein.

Kits

The invention includes kits which allow the interchangeable use of a DNA library in more than one application. The kits provide primers which allow efficient transfer of a library element encoding region from a first vector to a second vector. The kits provide primers having a first region homologous with the linker sequence used in the construction of the DNA library and a second region homologous with either a first or a second region in a vector molecule required for a particular application. The kit can include the primers, e.g., arranged according to which DNA library or vector they are homologous with, as well as one or more of the following: buffers, enzymes, the library inserted in the first vector, the (second) vector into which the library is to be inserted, and instructions for use of the kit. The contents of the kit can be packaged in a suitable container.

The kit can include the library in a first vector, and primers for inserting it into a second vector. The second vector can also be included.

For example, the kit can provide primers suitable for introduction of existing DNA libraries into the pGAD424 vector, so that the libraries can be screened in a two-hybrid assay. In such a case the PCR primers could have a sequence of 5'-GAATTCNNNNNNN-3' (SEQ ID NO:9) and 5'-AGATCTNNNNNNN-3' (SEQ ID NO:10), where the GAATTC and AGATCT sequences correspond to the EcoRI and BglII sites, respectively, present in the polylinker region of the pGAD424 vector, and the NNNNNNN sequences correspond to the sequences of the linkers used in the construction of an existing DNA library (which can be the same or different). These sequences can vary depending on which DNA library is used. For example, when the Clonetech human brain (cat# HL4004AH), human bone marrow (cat# HL4022AB), human lymph node (cat# HL4023AB), human fetal liver (cat# HL4029AH), or mouse 11-day embryo (cat# ML4005AB) MATCHMAKER cDNA libraries are used, the NNNNNNN sequences will correspond to: AATTCGCGGCCGCGTCGAC (SEQ ID NO: 11) the nucleotide sequence of the EcoRI-NotI-SalI adaptor built in these cDNA libraries.

Primers of the invention allow small amounts of an existing DNA library constructed for a particular application, to be transferred into a different vector molecule and/or host cell suitable for another application. A simple PCR amplification, using the appropriate primers provided in the kit, followed by transfection of the nucleic acid insert molecule and the vector molecule into a host cell would result in the production of the desired DNA library.

The following examples which further illustrate the invention should not be construed as limiting.

EXAMPLES

1. GAP Repair Cloning Using Different Sizes of Overlap of DNA Sequences Between the MXI1 cDNA and the pJG-4.5 Yeast Vector.

In this example, the minimum overlap homology required for successful gap repair cloning was determined. The Mxi1 cDNA (Zervos A. S. et al. Cell, 75:223–232, 1993), coding the short form of Mxi1 protein of 191 amino acids, cloned unidirectionally into the EcoRI/XhoI sites of the pJG 4-5 yeast expression vector (pTZ10.1) was used. The pJG 4-5 vector (see FIG. 1) contains a nuclear localization sequence to maximize intranuclear concentration, the B42 transcription activation domain, a hemagglutinin epitope (HA) to facilitate detection, an ADH1 transcription terminator, a 2μ origin of replication, a TRP1+ selectable marker, and a GAL1 inducible promoter that drives the expression of the chimeric gene.

Using different PCR primers, increasing stretches of vector flanking sequence were added to both the 5' and 3' ends of the Mxi1 DNA. The 5' primers corresponded to the sequence of the HA tag and the GAL-1 promoter and the 3' end primers encoded sequence from the ADH terminator. Primers that added 50 (SEQ ID NOs: 1 and 2), 40 (SEQ ID NOs:3 and 4), 30 (SEQ ID NOs:5 and 6) and 20 (SEQ ID NOs:7 and 8) bp of vector sequence to the ends of the Mxi1 cDNA were used. The Mxi1 PCR product was then transfected into yeast used in a modified two-hybrid system (Gyuris J. et al. Cell, 75:791–803, 1993) together with the pJG4-5 plasmid that had been linearized using EcoRI and XhoI restriction enzymes. The yeast were plated onto selective plates lacking Ura-His-Trp- and two days later colonies appeared.

Figure 2:
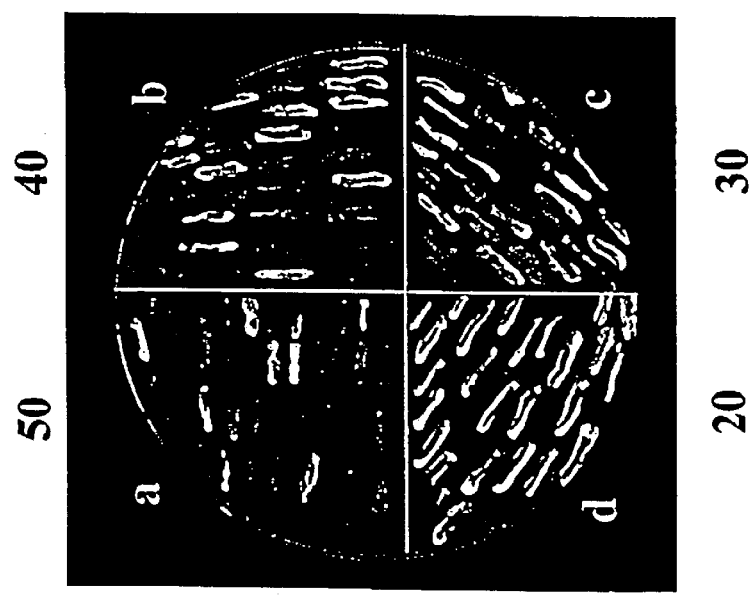
FIG. 2 is a depiction of the results of a stepwise decrease in the size of the overlap, from 50 bp to 20 bp (a–d), between the template (Mxi1) and the linear vector. The number of white yeast colonies increases as the homology is gradually reduced, indicating a non-productive gap repair process.

Successful gap repair was monitored by plating yeast on X-gal plates. Mxi1 that has been successfully incorporated into the yeast expression plasmid will form an Mxi1 fusion protein which will interact with the LexA-Max bait, already present in the yeast strain, and the yeast will turn blue. Incomplete gap repair will lead to an Mxi1 sequence out of frame with the vector sequence, and the yeast colonies will appear white. FIG. 2 shows the results obtained from this assay. The number of white yeast colonies increases as the size of the overlap is reduced from 50 bp to 20 bp (a–d) between the template (Mxi1) and the linear vector, indicating a non-productive gap repair process. These results show that a minimum overlap homology of 30 bp on both the 5' as well as the 3' end of the template and the linear plasmid should be used for successful gap repair cloning.

PCR amplification and addition of the flanking sequences was performed essentially as follows. The oligos used for PCR were:

5' GAG ATG CCT CCT ACC CTT ATG ATG 3'–50 (SEQ ID NO:1)

5' GAT TGG ACA CTT GAC CAA ACC TCT 3'+50 (SEQ ID NO:2)

5' CTA CCC TTA TGA TGT GCC AGA TTA 3'–40 (SEQ ID NO:3)
5' TTG ACC AAA CCT CTG GCG AAG AAG 3'+40 (SEQ ID NO:4)
5' GAT GTG CCA GAT TAT GCC TCT CCC 3'–30 (SEQ ID NO:5)
5 CTC TGG CGA AGA AGT CCA AAG CT 3'+30 (SEQ ID NO:6)
5' GAA GTC CAA AGC TTG AG 3'+20 (SEQ ID NO:7)
5' ATT ATG CCT CTC CCG 3'–20 (SEQ ID NO:8)

The 5' end corresponds to the DNA sequence upstream of the EcoRI cloning site of the pJG5-4 and encodes part of the transcription activator and the HA epitope tag. The 3' end corresponds to part of the ADH terminator sequence of the vector. PCR was performed using 10 ng of pTZ-Mxi1 as template and 100 ng each of the two primers in a 50 µl reaction volume. A program of 24 cycles was used consisting of: 30 seconds at 94° C., 1 minute at 65° C. and 1 minute at 72° C. The PCR product was gel purified, ethanol precipitated, resuspended in 50 µl TE and 5 µl was used along with 100 ng of linear plasmid to transform yeast using a variation of the lithium acetate method (Ito H. et al. *J. Bacteriol.*, 153:163–168, 1983).

2. Preparation of cDNA for in Vivo Cloning 30 bp of vector flanking sequences were added to both the 5' and 3' ends of a commercially available cDNA library (Marathon-Ready cDNA, Clontech, Ca# 7440-1) by PCR, using primers [5' GAT GTG CCA GAT TAT GCC TCT CCC GAA TTC <u>GCCGCC CGG GCA GGT</u> 3'] (SEQ ID NO:9) and [5'CTC TGG CGA AGA AGT CCA AAG CTT CTC GAG <u>TTC TAC AAT TCA GCG</u> 3'] (SEQ ID NO:10). Underlined regions of these primers are complementary sequences to the 5' and 3' ends of the linkers used during synthesis of the cDNA (Clontech) and the rest corresponds to the flanking DNA sequence 5' and 3' of the EcoRI and XhoI cloning sites of the pJG4-5 vector. PCR was performed in 50 µl reactions containing 5 µl of the cDNA and 250 ng of each of the two primers, using a PTC-100 TM (MJ Research-Inc.) cycler, programmed for 3 minutes at 94° C., followed by 30 cycles consisting of 30 seconds at 94° C., 30 seconds at 56° C. and 3 minutes at 68° C. The PCR amplified cDNA was ethanol precipitated, resuspended in the original volume with TE buffer and different amounts were used along with 0.5 µg of linear pJG4-5 vector to transform yeast strain. Using 0.5 µg of vector, maximum transformation efficiency was obtained with 10–15 µl of the PCR amplified cDNAs.

Colonies appeared after two days. Linear vector alone gave very few colonies whereas transformation efficiencies greater than $10^5$ per µg of linear vector were obtained with gap vector and cDNA. Several independent yeast colonies were isolated, grown overnight in liquid media and used to extract the pJG4-5-cDNA plasmid.

3. Characterization of cDNAs Isolated After in Vivo Cloning

In this example, the number of copies and the size of the different cDNAs cloned in vivo was characterized. Each yeast clone contained only a single plasmid which represented a successful gap repair of a unique cDNA and the vector.

Nine yeast colonies were randomly picked, grown overnight in liquid media and used to extract the pJG4-5-cDNA plasmid by standard procedures (Zervos A. S. et al. *Cell*, 75:223–232, 1993). Using primers [5' GAT GTG CCA GAT TAT GCC TCT CCC 3'–30] (SEQ ID NO:5) and [5' CTC TGG CGA AGA AGT CCA AAG CTT 3'+30] (SEQ ID NO:6), flanking the cDNA, the inserts were amplified by PCR, digested with restriction enzymes and analyzed on a 1% agarose gel. The clones had cDNA inserts varying in size from 300 bp to 2.3 kb (see FIG. 3, the marker used was a lambda DNA-BstEII digest). This result shows that the in vivo cloning method of the invention does not preferentially clone a particular size of cDNAs. All nine inserts were partially sequenced and found to represent different distinct cDNAs.

Equivalents

Those skilled in the art will recognize, or be able to ascertain, using no more than routine experimentation, many equivalents to the specific embodiments of the invention described herein. Such equivalents are intended to be encompassed by the following claims.

What is claimed is:

1. A method for constructing a DNA library in vivo, comprising:
   providing a plurality of host cells;
   providing a vector molecule having a first region and a second region;
   providing a plurality of nucleic acid insert molecules, each of the plurality of nucleic acid insert molecules having a first common region which is homologous with said first region of the vector molecule, a second common region which is homologous with said second region of the vector molecule, and a library element encoding region disposed between said first common region and said second common region, wherein when the library element encoding region encodes a naturally occurring sequence, the first and second regions are not naturally found adjacent to the library element encoding region;

introducing the vector molecule into each host cell of the plurality of host cells;

introducing a nucleic acid insert molecule from said plurality of nucleic acid insert molecules into each host cell of said plurality of host cells, wherein a different library element encoding region is introduced into each host cell of said plurality of host cells;

allowing homologous recombination and gap repair between a vector molecule and only one nucleic acid insert molecule to occur, and generating a plurality of vector molecules from said plurality of host cells, each vector molecule of the plurality comprising a different library element encoding region, and each vector comprising only one library element encoding region, thereby constructing a DNA library.

2. A method of constructing a DNA library, comprising:

providing a plurality of nucleic acid molecules wherein each of said nucleic acid molecule includes, in order from 5' to 3', a first common sequence, a library element encoding region, and a second common sequence;

providing a plurality of first primers, each of said first primers having a first region which hybridizes to the first common sequence of the nucleic acid molecule and having a second region which does not hybridize to said first or second common sequence;

providing a plurality of second primers, each of said second primers having a first region which hybridizes to the second common sequence of the nucleic acid molecule and having a second region which does not hybridize to said second or first common sequence;

forming a reaction mixture which includes said plurality of nucleic acid molecules, said plurality of said first primers, and said plurality of said second primers, under conditions which provide a plurality of nucleic acid insert molecules having the following structure, in order from 5' to 3', a second region of said first primer/said first common region/a library element encoding region/said second common region/a second region of said second primer;

providing a plurality of host cells;

providing a vector molecule having a first region which is homologous with said second region of said first primer, and a second region which is homologous with said second region of said second primer;

introducing said vector molecule into each host cell of the plurality of host cells;

introducing one or more of nucleic acid insert molecules from said plurality of nucleic acid insert molecules into each host cell of the plurality of host cells;

allowing homologous recombination and gap repair to occur between a vector molecule and only one nucleic acid insert molecule; and generating a plurality of vector molecules from said plurality of host cells, each vector molecule of the plurality comprising a different library element encoding region, and each vector comprising only one library element encoding region, thereby providing a DNA library.

3. The method of claim 2, wherein said first and second common sequences are the same.

4. The method of claim 2, wherein said first and second common sequences are different.

5. The method of claim 1, wherein said host cell is a yeast cell.

6. The method of claim 1, wherein said host cell is a bacterial cell.

7. The method of claim 1, wherein said at least one vector is linearized prior to being introduced into said host cell.

8. The method of claim 7, wherein said vector is linearized by cleaving between said first and second regions of said vector.

9. The method of claim 1, wherein said second common region of said nucleic acid insert molecule is produced by PCR.

10. The method of claim 1, wherein said first common region of said nucleic acid insert molecule is produced by PCR.

11. The method of claim 1, wherein said second common region of said nucleic acid insert molecule is produced by the ligation of adapters.

12. The method of claim 1, wherein said first common region of said nucleic acid insert molecule is produced by the ligation of adapters.

13. The method of claim 1, wherein said first and second common regions of said nucleic acid insert molecule are at least 30 base pairs in length.

14. The method of claim 1, wherein said first and second regions of said nucleic acid insert molecule are at least 40 base pairs in length.

15. The method of claim 1, wherein said first and second regions of said nucleic acid insert molecule are at least 50 base pairs in length.

16. The method of claim 1, wherein said library element encoding region is obtained from a cDNA library other than the one being constructed.

17. The method of claim 16, wherein said library element encoding region is obtained from a cDNA library which is plasmid based.

18. The method of claim 16, wherein said library element encoding region is obtained from a cDNA library which is phage based.

19. The method of claim 1, wherein said library element encoding region is obtained from an mRNA molecule.

20. The method of claim 19, wherein said mRNA molecule is obtained from a cancerous tissue.

21. The method of claim 1, wherein said DNA library is screened in a two-hybrid system and wherein said vector includes a transcription factor activation domain.

22. The method of claim 21, wherein said method further comprises, introducing into each host cell of said plurality of host cells a nucleic acid molecule encoding a hybrid protein, wherein the hybrid protein comprises a transcription factor DNA-binding domain attached to a test protein;

introducing into each host cell of said plurality of host cells a detectable gene, wherein said detectable gene comprises a regulator site recognized by said DNA-binding domain and wherein said detectable gene expresses a detectable protein when said test protein interacts with a protein encoded by the DNA library;

plating each host cell of said plurality of host cells onto selective media; and selecting for each host cell of said plurality of host cells containing a DNA encoded protein which interacts with test protein.

23. The method of claim 1, wherein said DNA library is used for screening and cloning of novel genes.

24. A method of constructing a DNA library for screening in a two-hybrid system, comprising:
   providing a plurality of nucleic acid molecules, wherein each of the plurality of nucleic acid molecules includes, in order from 5' to 3', a first common sequence, a library element encoding region, and a second common sequence;
   providing a plurality of first primers, each of said first primers having a first region which hybridizes to said first common sequence of said nucleic acid molecule and having a second region which does not hybridize to said first or second common sequence;
   providing a plurality of second primers, each of said second primers having a first region which hybridizes to said second common sequence of said nucleic acid molecule and having a second region which does not hybridize to said second or first common sequence;
   forming a reaction mixture which includes the plurality of nucleic acid molecules, the plurality of said first primers, and the plurality of said second primers, under conditions which provide a plurality of nucleic acid insert molecules having the following structure, in order from 5' to 3', a second region of the first primer/the first common region/a library element encoding region/the second common region/a second region of the second primer;
   providing a plurality of host cells;
   providing a vector having a first region which is homologous with the second region of the first primer, and a second region which is homologous with the second region of the second primer, wherein said vector further includes a transcription factor activation domain;
   introducing the vector molecule into each host cell of said plurality of host cells;
   introducing one or more of the nucleic acid insert molecules into each host cell of said plurality of host cells under conditions which allow for recombination and gap repair to occur;
   allowing homologous recombination and gap repair to occur between a vector molecule and only one nucleic acid insert molecule in each host cell of the plurality of host cells, wherein each host cell of the plurality comprises a vector molecule that comprises (a) a different nucleic acid insert molecule library element encoding region, and (b) only one library element encoding region,
   introducing into each host cell of said plurality of host cells a nucleic acid molecule encoding a hybrid protein, wherein the hybrid protein includes a transcription factor DNA-binding domain attached to a test protein;
   introducing into each host cell of said plurality of host cells a detectable gene, wherein said detectable gene comprises a regulator site recognized by the DNA-binding domain and wherein said detectable gene expresses a detectable protein when the test protein interacts with a protein encoded by the DNA library;
   plating each host cell of said plurality of host cells onto selective media; and
   selecting for each host cell of said plurality of host cells containing a DNA encoded protein which interacts with test protein.

* * * * *

SEQUENCE LISTING

```
<160> NUMBER OF SEQ ID NOS: 13

<210> SEQ ID NO 1
<211> LENGTH: 24
<212> TYPE: DNA
<213> ORGANISM: Unknown
<220> FEATURE:
<223> OTHER INFORMATION: primer_bind

<400> SEQUENCE: 1
gagatgcctc ctacccttat gatg                                          24

<210> SEQ ID NO 2
<211> LENGTH: 24
<212> TYPE: DNA
<213> ORGANISM: Unknown
<220> FEATURE:
<223> OTHER INFORMATION: primer_bind

<400> SEQUENCE: 2
gattggacac ttgaccaaac ctct                                          24
```

<210> SEQ ID NO 3
<211> LENGTH: 24
<212> TYPE: DNA
<213> ORGANISM: Unknown
<220> FEATURE:
<223> OTHER INFORMATION: primer_bind

<400> SEQUENCE: 3
ctacccttat gatgtgccag atta                                          24

<210> SEQ ID NO 4
<211> LENGTH: 24
<212> TYPE: DNA
<213> ORGANISM: Unknown
<220> FEATURE:
<223> OTHER INFORMATION: primer_bind

<400> SEQUENCE: 4
ttgaccaaac ctctggcgaa gaag                                          24

<210> SEQ ID NO 5
<211> LENGTH: 24
<212> TYPE: DNA
<213> ORGANISM: Unknown
<220> FEATURE:
<223> OTHER INFORMATION: primer_bind

<400> SEQUENCE: 5
gatgtgccag attatgcctc tccc                                          24

<210> SEQ ID NO 6
<211> LENGTH: 24
<212> TYPE: DNA
<213> ORGANISM: Unknown
<220> FEATURE:
<223> OTHER INFORMATION: primer_bind

<400> SEQUENCE: 6
ctctggcgaa gaagtccaaa gctt                                          24

<210> SEQ ID NO 7
<211> LENGTH: 17
<212> TYPE: DNA
<213> ORGANISM: Unknown
<220> FEATURE:
<223> OTHER INFORMATION: primer_bind

<400> SEQUENCE: 7
gaagtccaaa gcttgag                                                  17

<210> SEQ ID NO 8
<211> LENGTH: 15
<212> TYPE: DNA
<213> ORGANISM: Unknown
<220> FEATURE:
<223> OTHER INFORMATION: primer_bind

<400> SEQUENCE: 8
attatgcctc tcccg                                                    15

<210> SEQ ID NO 9
<211> LENGTH: 13
<212> TYPE: DNA
<213> ORGANISM: Unknown
<220> FEATURE:

-continued

```
<223> OTHER INFORMATION: primer_bind
<221> NAME/KEY: misc_feature
<222> LOCATION: (1)...(13)
<223> OTHER INFORMATION: n = A,T,C or G

<400> SEQUENCE: 9
gaattcnnnn nnn                                              13

<210> SEQ ID NO 10
<211> LENGTH: 13
<212> TYPE: DNA
<213> ORGANISM: Unknown
<220> FEATURE:
<223> OTHER INFORMATION: primer_bind
<221> NAME/KEY: misc_feature
<222> LOCATION: (1)...(13)
<223> OTHER INFORMATION: n = A,T,C or G

<400> SEQUENCE: 10
agatctnnnn nnn                                              13

<210> SEQ ID NO 11
<211> LENGTH: 19
<212> TYPE: DNA
<213> ORGANISM: Unknown
<220> FEATURE:
<223> OTHER INFORMATION: primer_bind

<400> SEQUENCE: 11
aattcgcggc cgcgtcgac                                        19

<210> SEQ ID NO 12
<211> LENGTH: 9
<212> TYPE: PRT
<213> ORGANISM: Unknown
<220> FEATURE:
<223> OTHER INFORMATION: domain
<221> NAME/KEY: VARIANT
<222> LOCATION: (1)...(9)
<223> OTHER INFORMATION: Xaa = Any Amino Acid

<400> SEQUENCE: 12

Cys Xaa Xaa Cys Xaa Cys Xaa Xaa Cys
  1               5

<210> SEQ ID NO 13
<211> LENGTH: 9
<212> TYPE: PRT
<213> ORGANISM: Unknown
<220> FEATURE:
<223> OTHER INFORMATION: domain
<221> NAME/KEY: VARIANT
<222> LOCATION: (1)...(9)
<223> OTHER INFORMATION: Xaa = Any Amino Acid

<400> SEQUENCE: 13

Pro Xaa Xaa Trp Xaa Trp Xaa Xaa Pro
  1               5
```